(12) United States Patent
Lee et al.

(10) Patent No.: US 6,994,842 B2
(45) Date of Patent: Feb. 7, 2006

(54) AEROGEL POWDER THERAPEUTIC AGENTS

(75) Inventors: Kang P. Lee, Sudbury, MA (US); George L. Gould, Mendon, MA (US)

(73) Assignee: Aspen Aerogels, Inc., Marlborough, MA (US)

( * ) Notice: Subject to any disclaimer, the term of this patent is extended or adjusted under 35 U.S.C. 154(b) by 0 days.

(21) Appl. No.: 10/034,444

(22) Filed: Dec. 21, 2001

(65) Prior Publication Data

US 2002/0094318 A1 Jul. 18, 2002

Related U.S. Application Data

(60) Provisional application No. 60/257,436, filed on Dec. 22, 2000.

(51) Int. Cl.
*A61K 9/12* (2006.01)
*A61K 9/14* (2006.01)
*A61K 9/16* (2006.01)

(52) U.S. Cl. .......................... 424/45; 424/46; 424/489; 424/450; 514/2

(58) Field of Classification Search ................. 424/45, 424/46, 9.51, 85.6, 489, 450; 428/403, 402.2; 514/2; 23/295
See application file for complete search history.

(56) References Cited

U.S. PATENT DOCUMENTS

| 5,864,923 | A | * | 2/1999 | Rouanet et al. ........... 23/295 R |
| 5,958,589 | A | | 9/1999 | Glenn et al. |
| 5,981,474 | A | * | 11/1999 | Manning et al. ................ 514/2 |
| 6,123,936 | A | * | 9/2000 | Platz et al. ................ 424/85.6 |
| 6,277,489 | B1 | * | 8/2001 | Abbott et al. ................ 428/403 |
| 6,403,056 | B1 | * | 6/2002 | Unger ....................... 424/9.51 |

FOREIGN PATENT DOCUMENTS

| AU | 199965549 A1 | 3/2000 |
| WO | WO 95/01165 A | 1/1995 |

* cited by examiner

*Primary Examiner*—Sreeni Padmanabhan
*Assistant Examiner*—Mina Haghighatian
(74) *Attorney, Agent, or Firm*—Townsend and Townsend and Crew LLP

(57) ABSTRACT

Drugs in the form of very fine highly porous aerogel particles are delivered to a patient via inhalation. The aerogel particles are either an aerogelized form of a pharmaceutical or deposited upon aerogel particles produced from a non-inorganic oxide carrier matrix material, e.g. a sugar or carbohydrate. The aerogel particles are readily dissolvable by the pulmonary surfactant present in the lungs of a mammal.

27 Claims, No Drawings

AEROGEL POWDER THERAPEUTIC AGENTS

This application claims benefit of 60/257,436, filed Dec. 22, 2000.

BACKGROUND OF THE INVENTION

The present invention is directed to an improved method of delivering pharmaco-therapeutic agents in which the time required for drug delivery into a patient's blood stream is substantially reduced. The delivery is direct to the blood stream, but non-invasive, non-disruptive, and pain-free. Examples of the classes of pharmaco-therapeutic agents which may be delivered in accordance with the present invention include such as: opioid-receptor agonists/antagonists, dopamine-receptor agonists/antagonists, serotonin-receptor agonists/antagonists, monoamine transporter agonists, antimanic agents, anti-smoking agents and immunogenic therapies (antibody products to reduce peripheral levels of drug substances), vaccines, antibiotics, high blood pressure drugs, heart medications, asthma medications, sexual dysfunction medications, analgesics, anesthesia drugs, insulin, and the like.

There are four general types of drug delivery currently available: oral, injection either intravenous, subcutaneous or transdermal, implants, and inhalation. Each of the methods has advantages and disadvantages.

1. Oral administration is acceptable in most cases except that the drug delivery rate is often too slow and it can cause digestive tract upset.

2. Intravenous injection is effective, but is intrusive, painful, has a danger of causing adverse reactions from the body due to a high concentration drug flowing through one small pathway, and presents a danger of infection both for the patient and the health-giver alike. Also if the injections have to occur frequently, such as once or twice a day for insulin as an example, there is a problem of running out of injectable locations let alone pain, bruises and danger of infections. Transdermal injection can be an answer to a lot of problems but has not been widely used. The technology is still in early stages of development.

3. Implants are used to avoid multiple shots and to maintain constant dosage over a long period of time, but requires invasive surgery.

4. Inhalation is an ideal drug delivery method. It can be done widely and conveniently because it is very fast and non-intrusive. Inhalants such as for asthma have shown a lot of promise but they are still not completely satisfactory. They take effect very rapidly, sometimes even faster than intravenous injection, but the inhalant method is currently limited to a few medications due to the difficulties of forming suitable dispersions for delivery into the lungs. Also most inhalants today use a chlorofluoro compound (CFC) as a dispersant and there is a movement to move away from CFC's for environmental reasons as well as suspected harmful effects that CFC's might have inside the body.

The development of the first pressurized metered dose inhaler (MDI) in the mid-1950s was a major advance in the administration of drugs locally to the lung, especially for the treatment of asthmatics. More recently, research has focused on using the lung as a conduit to deliver biomolecules such as peptides and proteins to the systemic circulation. Sophisticated dry powder inhaler (DPI) and metered solution devices have also been designed, both to improve deep-lung delivery and to address the MDI actuation/breath coordination issue that is problematic for certain patients. Relatively little development effort has been applied to improve pulmonary drug delivery by means of new formulation strategies.

One attempt to produce an improved inhalant drug delivery system is that of Alliance Pharmaceutical which is based upon "PulmoSpheres" which are prepared by mixing a drug and a surfactant to form an emulsion and then spray-drying the emulsion to cause the drug to be encased in the shells of hollow, porous, microscopic surfactant spheres. The resultant powder is then suspended in a fluorochemical or other propellant or carrier for delivery of the drug medications into the lungs or nasal passages of a patient. The hollow/porous morphology of the microspheres allows non-aqueous liquid propellants such as fluorochemicals to permeate within the particles, improving suspension stability and flow aerodynamics while impeding particle aggregation. U.S. Pat. No. 6,123,936 utilizes this technology to produce a dry powder formulation for interferons. Use of the spray-drying process precludes the preparation of products from any heat-sensitive pharmaceuticals since the drying must be conducted at elevated temperature, i.e. about 50 to 200° C. (122–392° F.)

Moreover, the densities of porous particles that can be produced by a spray-drying process, although much lower than many currently available solid or liquid inhalant particles, are still too high for many uses resulting in too much of the drug which is being delivered not reaching the lung surfaces.

The porosity and surface area of the aerogel products of this invention are much higher than those of spray-dried particles. The density of the aerogel products, which can be as low as about 0.003 g/cc, is much lower than both the PulmoSpheres (about 0.1 g/cc) and that of crystalline powders (about 1 g/cc). As a result, the aerogel inhalants of this invention float much longer resulting in more pharmaceutical material reaching the inner part of lungs. Thus the delivery efficiency is improved.

Although the primary intended use of aerogels heretofore has been in the field of insulation, some inorganic oxide aerogels have been used as carriers for the delivery of agricultural, veterinary medicines, and pharmaceuticals. For example, Australian Patent 711,078 discloses the use of aerogels prepared from inorganic oxides like silica by surface modifying them for hydrophobicity and then use as carriers in agricultural and veterinary medicine, i.e. to carry an active material such as insecticides, nematicides, etc. as well as viruses, bacteria, and other microorganisms. Australian Patent 9965549 discloses the use of inorganic aerogels as carriers for pharmaceutically active compounds and preparations as solid, semisolid and/or liquid oral preparations.

None of the prior aerogels and uses thereof are related to aerogel particles which are soluble in pulmonary surfactant or the use of such particles as a dosage form for delivery of a pharmaceutical by inhalation as in the present invention.

It is an object of this invention to substantially increase the applicability of inhalation drug delivery to wider class of drugs by producing them in the form of aerogel powders.

It is a further object of this invention to formulate an aerogel powder form of a drug so that it is capable of reaching much of the available mucous area inside the lungs.

It is a further object of this invention to formulate an aerogel powder form of a drug for quick dissolution and introduction into the blood stream of mammals and quick release of the drug.

It is a further object of this invention to formulate an aerogel powder form of a drug for quick introduction into the blood stream of mammals and controlled release of the drug thereafter.

It is a further object of this invention to formulate an aerogel powder form of a drug for a long shelf life by making it physico-chemically stable in its composition and packaging.

It is a further object of this invention to produce devices and equipment suitable for delivery of an aerogel powder form a drug.

It is a further object of this invention to produce a controlled drug administration environment, e.g. room, in which drug delivery may be done passively, without coercion, man-handling, or intrusive measures.

SUMMARY OF THE INVENTION

This invention is directed to an aerogel powder form of a pharmaco-therapeutic agent for use as an inhalant for mammals including humans.

More specifically, in one embodiment the invention involves preparing highly porous, low density, micron sized aerogel particles directly from the therapeutic substance of interest as an inhalant. In a second embodiment, wet ultra-fine porous gels are prepared from a material which is soluble in pulmonary surfactant, if necessary the solvent used to prepare the wet gels is exchanged for a solvent in which the therapeutic agent is dissolved, then a solution of the therapeutic agent in a solvent is penetrated into the pores of the wet gel by soaking until the desired deposition occurs, and the aerogels formed by supercritical drying. In both embodiments the resulting aerogels are then milled to the desired final particle size.

The aerogel particles of the present invention exhibit a low density (down to about 0.003 g/cc), an extremely high porosity (up to about 95%), a high surface area (up to about 1000 $m^2/g$) and a small particle size (micron sized and below). As a result of these properties, a pharmaceutical in the form of an aerogel powder results in a non-invasive high rate drug delivery system. The aerogel powders are in the form of extremely light, ultra-fine particles which will be easily airborne for an extended time during inhalation before settling down by gravity. This enables them to reach the innermost alveoli of the lungs and deliver the drug into the blood stream very rapidly.

DESCRIPTION OF THE PREFERRED EMBODIMENTS

The inhalable aerogel particle drug delivery method of the present invention is applicable to the preparation and use of inhalable forms of common therapeutic drugs such as insulin, aspirin, Viagra®, asthma medication, cold medication, antibiotics, etc. The drugs are delivered into the blood stream of a patient at a delivery rate well exceeding the drug delivery rate of intravenous injection and without the sting of a needle. The aerogel particle method bypasses potential problems with the digestive system and enables the medication to take effect at a much faster rate than is possible today.

Examples of substances that can be produced in the aerogel form of the present invention include but is not limited to: methadone, Orlaam®, Buprenorphine®, nicotine, other opioid-receptor agonists/antagonists, dopamine-receptor agonists/antagonists, serotonin-receptor agonists/antagonists, monoamine transporter agonists, anti-manic agents, anti-smoking agents and immunogenic therapies (antibody products to reduce peripheral levels of drug substances), vaccines, antibiotics, high blood pressure drugs, heart medications, asthma medications, sexual dysfunction medications, analgesics, anesthesia drugs, diabetic medications, and the like.

Particularly suitable substances are those useful in drug treatment programs. Methadone, a synthetic narcotic, which has been used for more than 30 years to treat heroin addiction by suppressing withdrawal symptoms and curbing the craving for heroin is particularly suitable. It is moderately soluble (12g/100 mL) in water, the preferred dosage vehicle since the mucous membrane transfers water to the particle on contact. Orlaam, another synthetic narcotic known generically as levomethadyl acetate, was approved in 1993, but has not been widely used. Buprenorphine, also a synthetic narcotic, is awaiting approval from the U.S. Food and Drug Administration for use as an anti-addiction drug. It causes weaker narcotic effects. No serious side effects are reported for any of the above three synthetic narcotics except for occasional constipation, nausea and dry mouth for some patients. Also, high dosages for all three were found to be much more effective in controlling the heroin addiction than low dosages.

Naltrexone is used to reduce alcohol cravings and to cause drinking to be less pleasurable (by inducing an unpleasant side effect such as nausea when ethanol consumption occurs). Naltrexone is a narcotic antagonist, which was originally used for narcotic dependency. Ethanol supposedly stimulates the body's natural opiates, and Naltrexone (or Revia) blocks this stimulation reducing cravings and pleasure. Naltrexone is only effective for 24 hours, thus a once daily dose is required. The pharmacokinetic efficacy of the drug is limited due to relatively slow absorption, thus making an alternative dosage to the solid pill form to deliver the drug rapidly to the bloodstream would have advantages.

Methadone and Naltrexone will be used as examples in the following description of how to prepare aerogel products of this invention. The aerogel forms of both drugs are sufficiently physicochemically stable to ensure adequate shelf life.

In general, the production of aerogels involves a sol-gel process during which a wet gel containing the substance of interest is formed with a proper solvent and catalyst. After the wet gel with nano-size pores and a lattice structure has been formed, a supercritical extraction process is used to supercritically dry the gel while avoiding potential collapse of the delicate pore and lattice structures due to the lack of surface tension of the supercritical fluid. Most commonly the supercritical fluid will be carbon dioxide ($CO_2$). The resulting dried gel exhibits nano-size pores (generally about 1 to 100 nm, preferably about 5 to 50 nm, more preferably about 10 nm), a high surface area (generally about 100 to 1,500 $m^2/g$, preferably about 100 to 1,200 $m^2/g$, more preferably about 500 to 1,000 $m^2/g$), a low density (generally about 0.1 to 0.0001 g/cc, preferably about 0.01 to 0.001, more preferably about 0.003 g/cc), and a small particle size (generally in the range from submicron up to about 2 microns).

Methadone hydrochloride is a synthetic narcotic analgesic commonly used to treat heroin addicts who would otherwise suffer narcotic withdrawal symptoms. Treatment consists of oral dosages of the soluble hydrochloride salt, which can be safely autoclaved for sterilization. The "free base" methadone has the chemical structure shown below on the right. It is likely to be the therapeutic agent, but is not water soluble. However, it is very soluble in non-polar organic solvents and fats, and should have appreciable solubility in liquid or supercritical carbon dioxide. The basicity of the molecule allows it to be readily protonated by strong acids to form an ammonium salt. The preferred form for handling is in the form of the ammonium salt, typically either as the hydrochloride shown on the left or as the sulfate (not drawn).

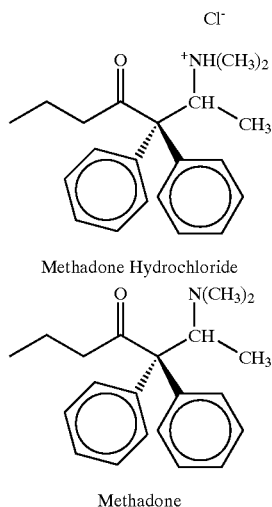

Methadone Hydrochloride

Methadone

The salts do not have appreciable solubility in non-polar organic solvents, but rather have excellent solubility in water and alcohols (one gram of the hydrochloride salt dissolves in 0.4 mL of water, 3.2 mL of cold water, 2 mL of hot ethanol, or 12 mL of chloroform).

The methadone aerogel powder may be formed by co-gelling the free base with glucose (which is preferably formed in situ from diisopropylidene glucose precursor and sacrificial 1,2-diols via a trans-acetalization reaction) in a solvent by the addition of a stoichiometric amount of anhydrous hydrogen chloride or hydrochloric acid. Varying the ratio of methadone to glucose in the solvent will allow control of the gelling behavior of the hydrochloride salts to produce desired physical characteristics while avoiding the formation of a dense methadone hydrochloride crystallization. If desired, the anion can be changed and/or other acids may be used to modify wet gel formation when reacted with the methadone/glucose precursor/solvent combination. Examples of suitable acids include mineral acids (hydrochloric, sulfuric, nitric) and organic acids (gluconic, malic, fumaric, citric). The variables that can be used to control the gelling reaction are solvent identity, 1,2-diol identity (e.g. 1,2-phenyl-ethanediol, 1,2-propanediol, glycerol), methadone concentration, acid identity, temperature, percentage of water present, and the like.

Supercritical drying of the gels with carbon dioxide gives aerogel powders with the highest possible surface area. The supercritical drying process may be performed in any well known conventional manner. Thus further details of the supercritical drying process are not provided herein. The supercritical drying is performed at a temperature below about 40° C.

Naltrexone aerogel powder in accordance with the present invention may be produced in the following manner. Generally, Naltrexone is provided in the form of a hydrochloride salt to improve solubility in water and hence bioavailability. The formation of a high surface area Naltrexone containing aerogel powder will be accomplished by co-gelling the hydrochloride or other suitable salt of the free base Naltrexone with glucose in a similar manner to that described above for methadone. The glucose gel will preferably be formed in situ from a solution of 1,2:5,6 di-O-isopropylidene a-gluco-furanose and an excess of sacrificial 1,2-diols via acid-catalyzed trans-acetalization in an appropriate solvent. The resulting product will have Naltrexone suspended in a glucose/solvent gel matrix. Subsequent drying with supercritical carbon dioxide will provide the high surface area aerogel powders. Varying the ratio of Naltrexone to glucose in a particular solvent will enable control of the gelling behavior of the hydrochloride salts to avoid dense Naltrexone hydrochloride crystallization. The anion can be changed as well, and a variety of acids can be investigated which may enhance wet gel formation when reacted with the Naltrexone/glucose precursor/solvent combination. Mineral acids (hydrochloric, sulfuric, nitric) and a modest sampling of organic acids (gluconic, malic, fumaric, citric) may be used. System variables that can be used to control gelling behavior include solvent identity, 1,2-diol identity (e.g. 1,2-phenylethanediol, 1,2-propanediol, glycerol), Naltrexone concentration, acid identity, temperature, percentage of water present and rheological control additives. Supercritical drying of the gels with carbon dioxide will give aerogel powders with the desirable properties specified above.

The free base is highly soluble in supercritical carbon dioxide but not that soluble in water. In case, a slower and longer duration release of the drug is desired, then the aerogels can be prepared using free base Naltrexone. In such a case, aerogelized free base Naltrexone can be prepared by adsorbing it onto a preformed appropriate aerogel, e.g. glucose, while in the supercritical $CO_2$ or other drying gas. This will be followed by depressurizing the system strategically to reduce the solute solubility and deposit the solute Naltrexone on the pores of the gels. Upon contact with pulmonary surfactant present on a patient's lung tissue, the glucose aerogel powder doped with the Naltrexone free base will dissolve rapidly, leaving behind tiny packets of free base Naltrexone directly on the lungs. The packets of these insoluble agents are so small that they simply diffuse across the membrane into the blood stream at a desired slow speed. Moreover, even after getting into the blood stream, the Naltrexone should metabolize much more slowly than conventional Naltrexone hydrochloride. This produces a dosage vehicle having a long duration bioavailability inside the human body after just a brief inhaling.

Alternatively, in a second embodiment shown in more detail in the Examples below, a therapeutic aerogel powder may be prepared by first forming porous gels from a carrier material which is soluble in pulmonary surfactant, e.g. a sugar or a carbohydrate. This reaction is usually carried out in a solvent. If that solvent will also dissolve the therapeutic agent, then a solution of the therapeutic agent is allowed to penetrate into the pores of the wet gel by soaking until the desired deposition has occurred. If the reaction solvent will not dissolve the therapeutic agent, then the solvent in the resulting gels is first removed by repeatedly exchanging the wet gels with the therapeutic agent solvent (or a close homologue thereof), generally at a temperature between about ambient and 50° C. for a period of about 3–10 hours, and then the therapeutic agent solution is allowed to penetrate the pores. Thereafter the aerogels are formed by supercritical drying at low temperature.

Further alternatively, in a third embodiment when the therapeutic agent is soluble in the reaction solvent, a solution thereof may be added prior to the initial gel formation to avoid the solvent exchange step. Such a process is likely to provide less control of the uniformity of the therapeutic agent deposition and thus is less preferred.

Since the small particle size and high open porosity are critical for fast and even solubility in pulmonary surfactant and absorption at the mucous membrane, the initial aerogel bodies produced by any of the embodiments are comminuted in any suitable manner. Smaller particle diameters can be obtained while maintaining the porous structure by utilizing conventional methods such as impact milling, ball milling, and jet milling. Jet milling in a spiral jet mill has been found capable of producing particles as small as 0.5 micron without lattice destruction or a substantial decrease in open porosity or increase in density. Below a certain size, further reduction may not be warranted since the suspension and dissolving properties of the aerogel particles are so excellent.

The air suspension characteristics of the micron and submicron size aerogel particles are determined using a small chamber with a paddle fan based upon the principle of the lower the minimum air speed necessary to keep the particles afloat substantially indefinitely, the greater the loft and travel of the particles within the air passages of a patient to the lungs. The mechanism of particles floating in the air can be explained as follows: the lift provided by the fluid drag force, that is proportional to the velocity squared, is balancing and overcoming the gravitational pull downward due to density difference between the fluid and the floating particles. The lower the density difference between the floating particle and the fluid, the higher the chances the particle will stay afloat at a given level of fluid motion and the particle dimension. Since the aerogel particles are so porous, up to 95% filled with the same fluid and therefore much lighter than a solid particle, they have much better chances of remaining afloat reaching the innermost part of the lungs and settling on the pulmonary surfactant rather than on the mucous membranes along the way. Since human lungs have an equivalent surface area of a tennis court, it is advisable to take advantage of as much of the surface of the lungs as possible for efficient drug delivery. In actual animal tests, as an animal breathes in air and the air reaches the alveoli, the air velocity begins to slow down and eventually goes to near zero. Therefore, minimum air speed necessary to keep the particles aloft in the particle test chamber is a good measure of how long and how far the particles would stay entrained in the air flow as the air goes through the air pipes and reaches the alveoli of the lungs.

Optionally, additives to reduce static electric charge on the aerogel particles may be used.

The aerogel powders dissolve very fast once exposed to pulmonary surfactant and the water on the mucous membranes. This is due to the aerogel powders having pores that are only a few nanometers in diameter. The capillary pressure is proportional to the surface tension of the fluid and inversely proportional to the characteristic dimension of the pores. The surface tension of water is very high and the same for both a sold particle and aerogel particle. However, the characteristic dimension for a solid particle is the diameter of the particle (e.g., 2.5 micrometer) whereas the characteristic dimension for an aerogel particle is the pore diameter (e.g., 2.5 nanometer). This means the capillary pressure to get the inside pores of an aerogel particle wet could be 1000 times higher than the surface tension force that tends to wet the surface of the solid particles. Combine this with the fact that once the pores of the aerogel particle are filled with the surfactant/water liquid, the dimensions or thickness of the solid material which must be dissolved into the liquid is only 1~2 nanometers thick, i.e. the aerogel lattice structure forming the pores, as opposed to the one or two micrometer radius of the particle. Thus the speed of dissolution could be 1,000 times faster for aerogel particles as opposed to solid particles.

Another way of looking at the fast dissolution of aerogel particles is based upon the surface area the particle which is exposed to solubilizing liquid. The surface area of a solid ball of 2.5 micrometer is $20 \times 10^{-12}$ $m^2$. For aerogel particle of the same diameter with a specific pore surface area of 1000 $m^2$/g and a density of 0.1 g/cc, the interior pore surface area is $8.2 \times 10^{-10}$ $m^2$. In other words, the surface area of an aerogel particle is approximately 42 times that of a similarly sized regular solid particles. Since all the pores of the aerogel particle will fill with surfactant/water, the dissolution occurs more rapidly. Therefore, the speed of dissolution of aerogel particles is at least two or three orders of magnitude faster than regular solid particles which means that there is a much faster absorption of the aerogel drug into the blood stream.

Inhalation of certain substances are known to reach the blood stream in 8 seconds: far faster than delivery by intravenous injection. Inhalation delivery via aerogel powder, with its inherently effective reach into alveoli, and extremely quick dissolution and absorption, is an effective, non-invasive and rapid way of administering drugs.

A lot of materials can be produced in aerogel form, including most of the inorganic and organic substances including alkaloids, organic salts, monomers, polymers, proteins, and carbohydrates. This covers a vast variety of medications, both man-made and extracted from natural products. Therefore, the method of aerogel powder inhalation can be utilized as a more effective and non-invasive alternative drug delivery method for treatment of wide variety of diseases and symptoms.

Further examples of aerogel inhalable particles include an inhalable form of insulin and other daily medications that are generally injected with hypodermic needles, such as various vaccines now given by hypodermic or transdermal injections; high blood pressure medications and other pills now taken orally, such as Viagra, that may cause undesirable stomach reactions or are slow to take effect; asthma treating inhalant and cold medicines that would penetrate deeper into the innermost alveoli of the lungs; and other cases where medication is desired to be introduced into the blood stream fast and without invasive or painful measures. In general, the aerogel powder inhalation will be a viable alternative to needle injection, transdermal injections using high speed particle impingement, electric potential, etc., and implantations of slow release capsules.

This drug delivery method produces inhalable forms of common therapeutic drugs such as insulin, aspirin, Viagra®, asthma medications, cold medications, antibiotics, and the like, as long as an aerogelized form of the drug can be produced. Bypassing digestive systems, the medication will take effect much faster and more effectively than is possible today either taken orally, by inhalation or intravenous injection with less trauma and side effects.

A convenient way of using the aerogel powder as inhalants is by means of a portable inhalation device similar to conventional asthma medication devices into which the proper amount of an aerogel powder form of a pharmaceutical will be placed and then shaken or electrostatically dispersed evenly before inhalation.

Another convenient way of using the proposed drug delivery method for treatment of addicts will be placing the subject in a room into which the right concentration of aerogel dust of the selected substance is injected for a required period to reach the target dosage. The size, porosity, and surface area of the particles determine the rate of dissolution of the particles on the surface of the lungs and the rate of diffusion into the blood stream. Once the particle properties are fixed, the rate of the drug delivery can be determined by the concentration of particles in the inhaled air. Other things being equal, the rate of drug delivery will depend on the particulate concentration in the air. The total dosage will depend on the concentration and the exposure duration. The dosage chamber can be designed in such a way that once the desired dosage is reached, before opening the chamber, the particles in the air may be removed by filtering through an aerogel blanket filter. The substances collected by the filter can be recycled.

In those cases where the pharmaceutical aerogel product has to be diluted by means other than airborne dust concentration and/or exposure duration for medical reasons such as toxicity of highly pure substances, a carrier aerogel matrix can be doped with an appropriate level of the pharmaceutical aerogel product. Any such carrier material will have to be completely innocuous and harmless to humans and dissolvable in water also.

Further details and explanation of the present invention may be found in the following specific examples, which describe the manufacture of aerogel products in accordance with the present invention and test results generated therefrom. All parts and percents are by weight unless otherwise specified.

EXAMPLE 1

An insulin containing low density aerogel is prepared by first forming an aerogel carrier powder by the transacetalation of a soluble derivatized mannitol compound in a solvent that does not dissolve deprotected mannitol. Deprotection initiates the formation of the gel. These reactions are carried out by combining a diisopropylidene (1,2,5,6-diisopropylidenemannitol) or dibenzylidene (1,3,4,6-dibenzylidenemannitol) derivative of mannitol with an excess amount of a soluble 1,2-diol compound (i.e. (±)-1 phenyl-7,2-ethanediol (PED)), p-toluenesulfonic acid catalyst (0.5–2%), and a non-polar aprotic solvent (toluene or dichloromethane). The solvent in the resulting gels is removed by repeatedly exchanging the wet gels with ethanol at a temperature between ambient and 50° C. for a period of 4–6 hours.

Insulin is penetrated into the pores of the wet gel by soaking the gel with an alcoholic solution of insulin at 37° C. until the desired deposition of insulin is reached.

The alcohol exchanged wet gels are then dried by $CO_2$ extraction at a pressure and temperature above the critical point (about 35° C. and 1250 psi) until all of the alcohol has been removed. The resulting aerogels have a density of 0.02–0.05 g/cm$^3$ depending on the relative amounts of starting sugar derivative and solvents utilized.

The dried aerogels are then milled to a uniform particle size of 2 to 4 microns, by fluid energy milling in a 100 AS Alpine Spiral Jet Mill. Filtered high purity $N_2$ gas (from liquid nitrogen boil-off) is used to drive the milling process and to cool the product and mill surfaces. The cooling is important to minimize destruction of the insulin structure. This milling process gives a high ultra-fine powder portion with sizes between 0.5 to 10 microns. This size range is useful for pulmonary drug delivery. The process is carried out in an inert atmosphere to minimize exposure to potentially active insulin powders.

The pulmonary drug delivery ability of these powders is tested by means of a standardized airway replica system of the nasal, oral, pharyngeal, laryngeal, tracheal, and bronchial regions of the human airways. Repeated deposition and distribution studies under exacting and consistent flow and volume conditions without subject variability are done. Gamma scintigraphy analyses are used to measure total, regional, and local deposition in the replicas. This allows for the precise standardized comparison of formulations and the influences of particle size and inhalation pattern in individuals of different sizes and ages.

The concentration and biological integrity of the insulin is determined by enzyme linked immunosorbant assay, (ELISA), and sodium dodecyl sulfate-polyacrylimide gel electrophoresis, (SDS-PAGE). The ELISA determines the concentration of insulin that has maintained in its active tertiary structure. The SDS-PAGE shows that no breakdown of the insulin occurs during the processing of the aerogel containing insulin.

To determine the biological activity of the insulin in the aerogel preparations, a competitive binding assay is used to quantify the binding and activation of the insulin receptor. Insulin receptor transfected NIH 3T3 fibroblasts are incubated in the presence of the reconstituted powders with varying concentrations of an anti-insulin receptor antibody, which blocks the binding insulin to its receptor. The rate of autophosphorylation of the insulin receptor is measured qualitatively and quantitatively by autoradiography of SDS-PAGE gels, and scintillation counting of the incorporated $^{32}P$ in each samples.

Speed of dissolution for the insulin containing aerogel powder is measured against that of a regular insulin powder, by having the powder land on simulated mucous membrane and observing the dissolution process under a microscope and also by measuring the pH of the solution immediately behind the membrane. Rate of dissolution in situ is determined by using a hydrogel coated pH electrode that is exposed to insulin aerogel powders. The pH change or glucose/lactose level change in case the glucose/lactose gel is used as a carrier gel as a function of time to give diffusion of insulin to electrode surface. Rate of powder dissolution to form solvated insulin is proportional to the pH change at the electrode surface. The larger, slower to dissolve compounds have a slower pH change.

The aerogel-insulin powder more rapidly dissolves in a more uniform manner than conventional insulin.

EXAMPLE 2

The procedure of Example 1 is repeated except the low density aerogel powder containing insulin is formed by the transacetalation of derivatized trehelose compounds instead of the derivatized mannitol compounds. Substantially similar results are obtained.

EXAMPLE 3

The procedure of Example 1 is repeated except the low density aerogel powder is made to further contain morphine.

The concentration and biological activity of the morphine in the aerogel preparations is determined by a competitive binding assay that quantitates the binding and activation of the opioid receptor. Cultured neural cells expressing the opioid receptor are incubated in the presence of the reconstituted powders with varying concentrations of an anti-morphine receptor antibody, which blocks the binding morphine to its receptor. The rate of autophosphorylation of the opioid receptor is measured qualitatively and quantitatively by autoradiography of SDS-PAGE gels, and scintillation counting of the incorporated $^{32}$P in each sample.

EXAMPLE 4

The procedure of Example 3 is repeated except but the low density aerogel powder containing insulin is formed by the transacetalation of derivatized trehelose compounds instead of the derivitized mannitol compounds. Substantially similar results occur.

EXAMPLE 5

The procedure of Example 1 is repeated, except the low density aerogel powder is made to contain Viagra™. Viagra™, chemical name 5-[2-ethoxy-5-(4-methyl-piperazin-1-ylsulfonyl)phenyl]-1-methyl-3-propyl-1,6-dihydro-7H-pyrazolo[4,3-d]pyrimidin-7-one, formula C22H30N6O4S, is a potent selective inhibitor of the enzyme phosphodiesterase-5 (PDE-5), which destroys cyclic guanosine monophosphate (cGMP), allowing cyclic GMP to persist, itself a dilator of blood vessels.

In order to determine the biological activity of the Viagra™ in the aerogel powder preparations, a competitive enzyme assay is used to quantitate the inactivation of the phosphodiesterase-5 enzyme. Cytosol homogenates from cells incubated in the presence of $^{32}$P-ATP are incubated in the presence of varying concentrations of the reconstituted powders. The rate of cyclic GMP elimination is measured quantitatively scintillation counting of the incorporated $^{32}$P in each sample.

EXAMPLE 6

The procedure of Example 5 is repeated except that the low density aerogel powder containing Viagra is formed by the transacylation of derivitized trehalose compounds instead of the derivitized mannitol compounds. Substantially similar results occur.

What is claimed is:

1. A method of treating a disease state responsive to treatment by a therapeutic agent comprising pulmonarily administering to the alveoli of a subject in need thereof a dispersible dry powder comprising
a therapeutically effective amount of a therapeutic agent in aerogel particles wherein said particles have a density of about 0.1 to 0.001 g/cc and particle size to permit them to reach the alveoli of a human subject's lungs upon inhalation.

2. The method of claim 1 wherein said particles deliver said agent into the bloodstream of said subject.

3. The method of claim 1, wherein the aerogel particles contain pores of about 1 to 100 nm.

4. The method of claim 1, wherein the aerogel particles have a surface area of about 100 to 1,200 m$^2$/g.

5. The method of claim 1, wherein the aerogel particles have a particle size of about submicron up to about 3 microns.

6. The method of claim 1, wherein the aerogel particles are a carrier selected from the group consisting of sugars and carbohydrates.

7. The method of claim 1, wherein the therapeutic agent is insulin.

8. The method of claim 1 wherein the therapeutic agent is methadone.

9. The method of claim 1, wherein the therapeutic agent is naltrexone.

10. The method of claim 1, wherein the powder is prepared from an aerogel prepared by supercritical drying at a temperature of less than 40° C.

11. The method of claim 10, wherein the powder is prepared from an aerogel prepared by co-gelling the therapeutic agent with a gel-forming material selected from the group consisting of sugars and carbohydrates.

12. A method of delivering a therapeutic agent to a subject, said method comprising administering to the alveoli of said subject a dispersible dry powder comprising a therapeutically effective amount of said therapeutic agent in aerogel particles wherein said particles have a density of about 0.1 to 0.001 g/cc and particle size to permit them to reach the alveoli of a human subject's lungs upon inhalation as an inhalant.

13. A method of delivering a therapeutic agent to the bloodstream of a subject, said method comprising administering to the alveoli of said subject a dispersible dry powder comprising a therapeutically effective amount of said therapeutic agent and aerogel particles wherein said particles have a density of about 0.1 to 0.001 g/cc and particle size to permit them to reach the alveoli of a human subject's lungs upon inhalation as an inhalant.

14. The method of claim 1 wherein said agent is adsorbed onto the structure of said particles.

15. The method of claim 1 wherein said particles are directly prepared from said therapeutic agent.

16. The method of claim 1 wherein the structure of said particles comprise said therapeutic agent.

17. The method of claim 1 wherein said powder is formulated for quick introduction into the bloodstream and controlled release thereafter.

18. The method of claim 1 wherein the powder is formulated for slow release.

19. The method of claim 12, wherein the powder is prepared from an aerogel prepared by supercritical drying at a temperature of less than 40° C.

20. The method of claim 12, wherein the powder is prepared from an aerogel prepared by co-gelling the therapeutic agent with a gel-forming material selected from the group consisting of sugars and carbohydrates.

21. The method of claim 12, wherein the aerogel particles contain pores of about 1 to 100 nm.

22. The method of claim 12, wherein the aerogel particles have a surface area of about 100 to 1,200 m$^2$/g.

23. The method of claim 12, wherein the aerogel particles have a particle size of about submicron up to about 3 microns.

24. The method of claim 12, wherein the aerogel particles are a carrier selected from the group consisting of sugars and carbohydrates.

25. The method of claim 12, wherein the therapeutic agent is insulin.

26. The method of claim 12, wherein the therapeutic agent is methadone.

27. The method of claim 12, wherein the therapeutic agent is naltrexone.

* * * * *